United States Patent
Yuan et al.

(10) Patent No.: US 10,733,731 B2
(45) Date of Patent: Aug. 4, 2020

(54) SYSTEM AND METHOD FOR PREPROCESSING CAPSULE ENDOSCOPIC IMAGE

(71) Applicant: Ankon Technologies CO., LTD., Wuhan (CN)

(72) Inventors: Wenjin Yuan, Wuhan (CN); Hao Zhang, Wuhan (CN); Hang Zhang, Wuhan (CN); Xinhong Wang, San Diego, CA (US); Xiaodong Duan, Pleasanton, CA (US); Guohua Xiao, Plano, TX (US)

(73) Assignee: Ankon Technologies CO., LTD, Wuhan (CN)

( * ) Notice: Subject to any disclaimer, the term of this patent is extended or adjusted under 35 U.S.C. 154(b) by 132 days.

(21) Appl. No.: 15/959,058

(22) Filed: Apr. 20, 2018

(65) Prior Publication Data
US 2018/0308235 A1    Oct. 25, 2018

(30) Foreign Application Priority Data
Apr. 21, 2017  (CN) .......................... 2017 1 0267329

(51) Int. Cl.
*G06T 7/00* (2017.01)
*G06T 7/70* (2017.01)
(Continued)

(52) U.S. Cl.
CPC ........ *G06T 7/0014* (2013.01); *A61B 1/00009* (2013.01); *A61B 1/041* (2013.01);
(Continued)

(58) Field of Classification Search
CPC ................. G06T 7/0014; G06T 7/70; G06T 2207/20081; G06T 2207/20076; G06T 2207/10016; G06T 2207/20024; G06T 2207/30096; G06T 2207/10068; G06T 7/0012; G06T 7/62; G06T 7/90; A61B 5/065; A61B 1/00009; A61B 5/073;
(Continued)

(56) References Cited

U.S. PATENT DOCUMENTS

| 8,768,017 B2* | 7/2014 | Kanda ................ A61B 1/00009 |
| | | 382/128 |
| 2005/0075537 A1* | 4/2005 | Chen ................... A61B 1/00009 |
| | | 600/109 |

(Continued)

*Primary Examiner* — Yon J Couso
(74) *Attorney, Agent, or Firm* — Pearl Cohen Zedek Latzer Baratz LLP

(57) ABSTRACT

A system and a method for preprocessing capsule endoscope images are provided. The capsule endoscopic image preprocessing system include an in vitro image removal module, an invalid image removal module, a digestive tract image classification module, a lesion and anatomical structure identification module, and a lesion and anatomical structure redundant image removal module. The capsule endoscopic image preprocessing system removes in vitro images and invalid images from capsule endoscopic images, classifies the capsule endoscopic images according to different parts of the digestive tract, identifies lesion and anatomical structures in the classified capsule endoscopic images; and removes redundant lesion and anatomical structure images according to the lesion and anatomical structures.

20 Claims, 5 Drawing Sheets

(51) Int. Cl.

| | |
|---|---|
| *G06K 9/46* | (2006.01) |
| *G06K 9/03* | (2006.01) |
| *A61B 1/04* | (2006.01) |
| *G06T 7/90* | (2017.01) |
| *G06K 9/62* | (2006.01) |
| *G06T 7/62* | (2017.01) |
| *A61B 5/07* | (2006.01) |
| *A61B 1/00* | (2006.01) |
| *A61B 5/06* | (2006.01) |
| *G06K 9/40* | (2006.01) |

(52) U.S. Cl.
CPC ............. *A61B 5/065* (2013.01); *A61B 5/073* (2013.01); *G06K 9/036* (2013.01); *G06K 9/40* (2013.01); *G06K 9/4628* (2013.01); *G06K 9/4647* (2013.01); *G06K 9/4652* (2013.01); *G06K 9/627* (2013.01); *G06K 9/6267* (2013.01); *G06T 7/62* (2017.01); *G06T 7/70* (2017.01); *G06T 7/90* (2017.01); *G06K 2209/05* (2013.01); *G06T 2207/10016* (2013.01); *G06T 2207/10068* (2013.01); *G06T 2207/20024* (2013.01); *G06T 2207/20076* (2013.01); *G06T 2207/20081* (2013.01); *G06T 2207/30096* (2013.01)

(58) Field of Classification Search
CPC ...... A61B 1/041; G06K 9/036; G06K 9/4647; G06K 2209/05; G06K 9/40; G06K 9/627; G06K 9/4628; G06K 9/4652; G06K 9/6267

See application file for complete search history.

(56) References Cited

U.S. PATENT DOCUMENTS

2012/0316421 A1* 12/2012 Kumar ............... A61B 1/00009
  600/407
2019/0188851 A1*  6/2019 Zouridakis ............ G06T 7/0012

\* cited by examiner

SYSTEM AND METHOD FOR PREPROCESSING CAPSULE ENDOSCOPIC IMAGE

CROSS-REFERENCE OF RELATED APPLICATIONS

This application claims priority to Chinese Patent Application No. 201710267329.8 filed on Apr. 21, 2017, the contents of which are incorporated by reference herein.

FIELD OF INVENTION

The present invention relates to the technical field of computer aided detection, and in particular to a system and method for preprocessing capsule endoscopic images.

BACKGROUND

In the operating procedures of existing wireless capsule endoscope, the looks and brief information (e.g. name, gender, cellphone number) of a subject, and the capsule information (serial number, battery level, etc.) are required to be captured in vitro. In addition, the levels of proficiency that operators have in instrument and capsule endoscope are different, and the levels of adaptation of subjects to capsule endoscope are different, so that the capsule may capture a large number of images in vitro.

These images prevent examination data from being inconsistent with the subject and facilitate data management. However, these in vitro images are useless for doctors in image reading. The main purpose of doctors is to examine whether there are abnormalities in the digestive tract of subject. A large amount of in vitro images can affect the efficiency of doctor in image reading.

For lesions (such as bleeding, polyps, ulcers, tumors, etc.) and specific anatomical structures (such as cardia, pylorus, etc.), the wireless capsule endoscope can capture multiple images continuously in the digestive tract, resulting in image redundancy. This also affect efficiency of doctor in image reading.

During image capturing, an empty stomach and distance between gastric walls may cause the images captured to be too bright or too dark. As a result, more invalid images can be obtained, affecting the efficiency of doctor in image reading.

SUMMARY OF THE INVENTION

An object of the present disclosure is to provide a capsule endoscopic image preprocessing system and method.

In order to solve the technical problem, the present disclosure discloses a capsule endoscopic image preprocessing system, comprising an in vitro image removal module, an invalid image removal module, a digestive tract image classification module, a lesion and anatomical structure identification module, and a lesion and anatomical structure redundant image removal module; wherein the in vitro image removal module removes in vitro images from capsule endoscopic images based on average grayscale values of the capsule endoscopic image, values of the most frequent color of the capsule endoscopic images, and area ratio of the most frequent color of the capsule endoscopic images; wherein the invalid image removal module removes invalid images from the capsule endoscopic images from which the in vitro images have been removed, wherein the invalid images are images which brightness is not in a preset brightness range; wherein the digestive tract image classification module classifies the capsule endoscopic images according to different parts of the digestive tract; wherein the lesion and anatomical structure identification module identifies lesion and anatomical structures in the classified capsule endoscopic images; and wherein the lesion and anatomical structure redundant image removal module removes redundant lesion and anatomical structure images according to the lesion and anatomical structures.

A method for preprocessing capsule endoscopic image using the system as described above is provided, comprising following blocks:

block S1: removes in vitro images from the capsule endoscopic images based on average grayscale values of the capsule endoscopic images, values of the most frequent color of the capsule endoscopic images, and area ratio of the most frequent color of the capsule endoscopic images; wherein the in vitro images are removed by:

process the first N frames of images to obtain the average grayscale value sequences of RGB channels $M^R(p_1, p_2, \ldots, p_i, \ldots, p_N)$, $M^G(p_1, p_2, \ldots, p_i, \ldots, p_N)$, and $M^B(p_1, p_2, \ldots, p_i, \ldots, p_N)$, the value sequences of the most frequent color $C(p_1, p_2, \ldots, p_i, \ldots, p_N)$, and the area ratio sequences of the most frequent color $S(p_1, p_2, \ldots, p_i, \ldots, p_N)$, wherein $p_i$ is image frame number;

determine whether the capsule endoscope has entered the body based on the value sequences of the most frequent color $C(p_1, p_2, \ldots, p_i, \ldots, p_N)$ to obtain an initial position 1; wherein the initial position is obtained by: determine whether the value of the most frequent color $C(p_c)$ in the image frame number of $p_c$ is less than a set threshold TC, calculate the number of images MC with the value of the most frequent color $C(p_{c+j})$ continuously less than TC after the image frame number $p_c$ when the value of the most frequent color $C(p_c)$ is less than TC, determine that the capsule has entered the body of subject when MC is greater than a set threshold TM1, and record the image frame number p as an initial position 1; wherein $p_{c+j}$ represents the image after $p_c$, and the value of j is [1, M];

determine whether the capsule endoscope is outside the body based on the area ratio sequences of the most frequent color $S(p_1, p_2, \ldots, p_i, \ldots, p_N)$ to obtain an initial position 2; wherein the initial position 2 is obtained by: process from the $N^{th}$ image forward to determine whether the maximum color value area ratio of the capsule endoscopic image in the frame number $p_s$ is greater than a set threshold TS, calculate the number of images MS with the area ratio of the most frequent color $S(p_{s-q})$ continuously greater than TS ahead of the image frame number $p_s$ when the area ratio of the most frequent color $S(p_s)$ is greater than the set threshold TS, determine that the image is an in vitro image when MS is greater than a set threshold TM2, and record the image frame number $p_c$ as the initial position 2; wherein $p_{s-q}$ represents the image ahead of $p_s$, and the value of s is $[1, M_a]$, wherein $M_a$=TM2;

identify in-vitro images based on changes in average grayscale values of the RGB channels from the image frame number $p_s$ to the image frame number $p_c$; wherein the in-vitro images are identified by: calculate the changes in average grayscale value of the RGB channels from the image frame number $p_s$ to the image frame number $p_c$ by a formula of $D^o(p_m) = M^o(p_m) - M^o(p_{m+1})$, wherein, o represents channel and the o channel o comprises channel R, channel G and channel B; $p_m$ is an image frame number between $p_s$ and $p_c$ and the value of m is [s,c−1], in which, s is the frame number $p_s$ and c−1 is the frame number $p_c$; determine whether the changes in average grayscale values of RGB channels $D^R(p_m)$, $D^G(p_m)$ and $D^B(p_m)$ comply with a set threshold TD, determine that the image frame number $p_m$ nearest to the image frame number p s is the dividing position for in-vivo and in vitro images when $D^R(p_m)$<TD, $D^G(p_m)$<TD and $D^B(p_m)$<TD;

block S2: remove invalid images from the capsule endoscopic images from which the in vitro images have been removed, wherein the invalid images are removed by:

convert the capsule endoscopic RGB image from which in vitro images have been removed to grayscale image gray, determine that a pixel is bright pixel when pixel gray(x,y) of the grayscale image gray is greater than YH, determine that a pixel is dark pixel when pixel gray(x,y) of the grayscale image gray is less than YL, tally the sum of number of bright pixels and dark pixels SHL, wherein SHL=sYL+sYH, in which sYL represents the number of dark pixels and sYH represents the number of bright pixels; and remove the grayscale image gray when SHL is greater than ST, wherein ST=0.7*SI, in which SI is the total number of pixels in the grayscale image;

block S3: use deep learning method based on a convolutional neural network model to classify the capsule endoscopic images according to different parts of the digestive tract;

block S4: use deep learning method to identify lesion and anatomical structure in the capsule endoscopic images;

block S5: identify lesion and anatomical structure images sequences from the capsule endoscopic image according to the lesion and anatomical structure, and retain images from the lesion and anatomical structure image sequences based on the position, size and contrast characteristics of lesion and anatomical structure, wherein the images are retained by:

calculate the score RP of the position of lesion and anatomical structure in each lesion and anatomical structure image of the lesion and anatomical structure images sequence, wherein the score RP represents the distance from lesion and anatomical structure to the center of corresponding image. and wherein the score RP is calculated by:

$$RP_i = 1 - \frac{\sqrt{\left(lx_i - \frac{W}{2}\right)^2 + \left(ly_i - \frac{H_1}{2}\right)^2}}{\frac{\sqrt{W^2 + H_1^2}}{2}},$$

wherein, W and $H_1$ represent the width and height of the lesion and anatomical structure image, i represents the serial number in the lesion and anatomical structure images sequence, $RP_i$ represents the score of the position of lesion and anatomical structure in the $i^{th}$ image, and $lx_i$ and $ly_i$ represent the center coordinates of the position of lesion and the anatomical structure in the $i^{th}$ lesion and the anatomical structure image;

calculate the score RS of the size of lesion and anatomical structure in each lesion and anatomical structure image of the lesion and anatomical structure images sequence, wherein the score RS is calculated by: $RS_i=SW_i \times SH_i$, wherein, $RS_i$ represents the score of the size of lesion and anatomical structure in the $i^{th}$ lesion and anatomical structure image of the lesion and anatomical structure images sequence, and $SW_i$ and $SH_i$ represent the width and height of lesion and anatomical structure in the $i^{th}$ lesion and anatomical structure image;

calculate the score RC of the region contrast of lesion and anatomical structure in each lesion and anatomical structure image of the lesion and anatomical structure images sequence, and wherein the score RC is calculated by:

$$RC_i = \sum_\delta \delta(j,k)^2 P_\delta(j,k),$$

wherein, $RC_i$ represents the score of region contrast of lesion and anatomical structure in the $i^{th}$ lesion and anatomical structure image of the lesion and anatomical structure images sequence, $\delta(j,k)=|gray(j)-gray(k)|$ represents the grayscale difference between neighboring pixels j and k, and $P_\delta(j,k)$ represent the probability of occurrence of the grayscale difference $\delta(j,k)$;

calculate the total score RT of lesion and anatomical structure image, wherein the score RT is calculated by:

$RT_i = RP_i \times RS_i \times RC_i$, wherein $RT_i$ represents the total score RT of the $i^{th}$ image; and select the image with the maximum RT value in the lesion and anatomical structure images sequence as the image to be retained after removal of redundancy.

DETAILED DESCRIPTION

The present disclosure, including the accompanying drawings, is illustrated by way of examples and not by way of limitation. It should be noted that references to "an" or "one" embodiment in this disclosure are not necessarily to the same embodiment, and such references mean at least one.

In general, the word "module," as used herein, refers to logic embodied in hardware or firmware, or to a collection of software instructions, written in a programming language. In one embodiment, the program language may be Java, C, or assembly. One or more software instructions in the modules may be embedded in firmware, such as in an EPROM. The modules described herein may be implemented as either software and/or hardware modules and may be stored in any type of non-transitory computer-readable medium or other storage device. Some non-limiting examples of non-transitory computer-readable media include CDs, DVDs, flash memory, and hard disk drives.

Figure 1:
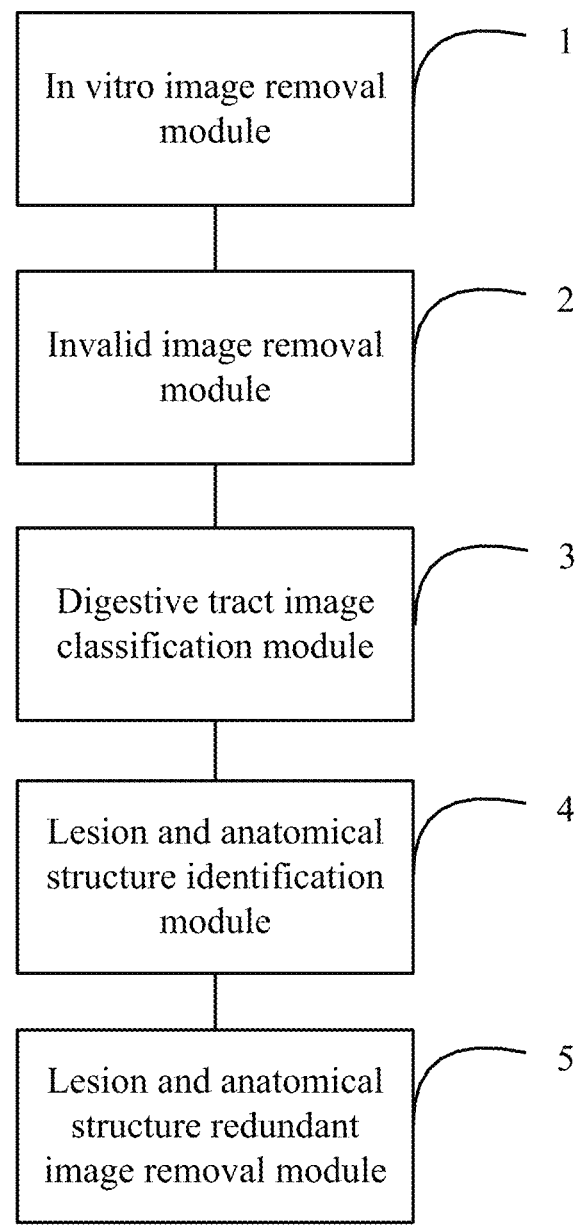
FIG. 1 shows a block diagram of one embodiment of a capsule endoscopic image preprocessing system.

An image preprocessing system and its preprocessing method are described in detail below. Elements in the drawings are 1 In vitro image removal module
2 Invalid image removal module
3 Digestive tract image classification module
4 Lesion and anatomical structure identification module 5 Lesion and anatomical structure redundant image removal module FIG. 1 shows a block diagram of one embodiment of a capsule endoscopic image preprocessing system. In one embodiment, the capsule endoscopic image preprocessing system comprises an in vitro image removal module 1, an invalid image removal module 2, a digestive tract image classification module 3, a lesion and anatomical structure identification module 4, and a lesion and anatomical structure redundant image removal module 5. The data output end of the in vitro image removal module 1 is connected to the data input end of the invalid image removal module 2. The data output end of the invalid image removal module 2 is connected to the data input end of the digestive tract image classification module 3. The data output end of the digestive tract classification module 3 is connected to the data input end of the lesion and anatomical structure identification module 4. The data output end of the lesion and anatomical structure identification module 4 is connected to the data input end of the lesion and anatomical structure redundant image removal module 5.

The in vitro image removal module 1 is configured to remove in vitro images from capsule endoscopic images based on average grayscale values of the capsule endoscopic images, values of the most frequent color of the capsule endoscopic images, and area ratio of the most frequent color of the capsule endoscopic images, and output the removed capsule endoscopic images to the invalid image removal module 2. The invalid image removal module 2 is configured to further process the capsule endoscopic images from which the in vitro images have been removed to remove invalid images, wherein the invalid images are images which brightness is not in the preset brightness range, and outputs the processed capsule endoscopic images to the digestive tract image classification module 3. The digestive tract image classification module 3 is configured to classify the processed capsule endoscopic images according to different parts of the digestive tract, and output the classified capsule endoscopic images to the lesion and anatomical structure identification module 4. The lesion and anatomical structure identification module 4 is configured to detect the classified capsule endoscopic images, and identify lesion and anatomical structures in the classified capsule endoscopic images, and output the identified lesion and anatomical structures to the lesion and anatomical structure redundant image removal module 5. The lesion and anatomical structure redundant image removal module 5 is configured to remove the redundant lesion and anatomical structure images according to the lesion and anatomical structures.

The average grayscale value of a capsule endoscopic image is calculated by:

$$M^o = \frac{1}{W \times H_1} \sum_{x=1}^{W} \sum_{y=1}^{H_1} I^o(x, y)$$

Wherein, W and $H_1$ represent the width and height of the capsule endoscopic image; $I^o(x,y)$ represents the grayscale value of o channels at the position image coordinates x and y. o channels represent R, G and B3 channels, and $M^o$ represents the mean value of o channels.

In one embodiment, a value of the most frequent color of the capsule endoscopic image is obtained as follows:

RGB channels in the capsule endoscopic image are converted into HSV channels. The conversion formula is:

$$H = \begin{cases} 0, & \text{if max} = \text{min} \\ 60 \times \frac{G-B}{\text{max}-\text{min}}, & \text{if max} = r \text{ and } g \geq b \\ 60 \times \frac{G-B}{\text{max}-\text{min}} + 360, & \text{if max} = r \text{ and } g < b \\ 60 \times \frac{B-R}{\text{max}-\text{min}} + 120, & \text{if max} = g \\ 60 \times \frac{R-G}{\text{max}-\text{min}} + 240, & \text{if max} = b \end{cases}$$

Wherein, max represents the maximum value among RGB channels; min represents the minimum value among RGB channels; the formula is used to calculate the value of hue H among HSV channels.

A histogram of the hue (H) among HSV channels is made statistics. The statistical formula is:

$$\text{hist}_k(H(x,y)) = \text{hist}_{k-1}(H(x,y)) + 1$$

Wherein, hist represents image histogram, H(x,y) represents the value of hue H at the position (x,y), k represents iterations (k<NUM, NUM represents the number of image pixels of the capsule endoscopic image).

The histogram hist(H(x,y)) of hue (H) among HSV channels is performed median filtering to remove interference.

A position corresponding to the maximum value Gaussian coefficient of the filtered histogram hist(H(x,y)) is obtained. The value of the color corresponding to the position is the value C of the most frequent color of the capsule endoscopic image.

In one embodiment, the maximum value Gaussian coefficient of the filtered histogram hist(H(x,y)) is calculated by: Perform non-linear least-square fitting for the histogram hist(H(x,y)) with Gaussian model. The fitting formula is:

$$f(hist) = \sum_{k=1}^{X} a_k e^{-\left(\frac{hist-c_k}{b_k}\right)^2}$$

Wherein, $a_k$ represents coefficient of the $k^{th}$ Gaussian model, and the value of k is 1~X; $b_k$ represents variance of the $k^{th}$ Gaussian model; $c_k$ represents mean value of the $k^{th}$ Gaussian model; X represents the number of Gaussian models; take $a_k$, and $c_k$ corresponding to the maximum coefficient $a_k$ (k is 1~X) is the value C of the most frequent color of the capsule endoscopic image.

In one embodiment, area ratio of the most frequent color of the capsule endoscopic image is obtained by: Binarize the hue H in HSV channels to obtain a binary image HB, wherein the threshold of binarization is TH (for example, TH=20), set the image to 1 as in vitro image if a binarization value of the image is greater than TH; otherwise set it to 0 as in vivo image. Accordingly, the area ratio of the most frequent color is:

$$S = \frac{1}{W \times H_1} \sum_{x=1}^{W} \sum_{y=1}^{H_1} HB(x, y)$$

Wherein, W and $H_1$ represent the width and height of the binary image; x and y represent pixel coordinates, and HB represents the binary image.

In one embodiment, the in vitro image removal module 1 removes in vitro images from the capsule endoscopic images based on the average grayscale values, the values of the most frequent color and the area ratio of the most frequent color. The in vitro image is removed as follows:

First, the in vitro image removal module 1 processes the first N frames of the capsule endoscopic images to obtain the average grayscale value sequences of RGB channels $M^R(p_1, p_2, \ldots, p_i, \ldots, p_N)$, $M^G(p_1, p_2, \ldots, p_i, \ldots, p_N)$, and $M^B(p_1, p_2, \ldots, p_i, \ldots, p_N)$, the value sequences of the most frequent color $C(p_1, p_2, \ldots, p_i, \ldots, p_N)$, and the area ratio sequences of the most frequent color $S(p_1, p_2, \ldots, p_i, \ldots, p_N)$. $p_i$ is image frame number. According to statistics on clinical case data, the value of N will not exceed 1000. In the embodiment, N=500, the image captured by the capsule endoscope just entering the body is generally red in hue, and H value of the red image is relatively small. Accordingly, threshold can be set to determine whether the capsule endoscope has entered the body and identify in vitro images to exclude.

Whether the capsule endoscope has entered the body is determined based on the value sequences of the most frequent color $C(p_1, p_2, \ldots, p_i, \ldots, p_N)$ to obtain the initial position 1. The initial position is obtained by: determine whether the value of the most frequent color $C(p_c)$ in the image frame number of $p_c$ is less than the set threshold TC (for example, TC=15). When the value of the most frequent color $C(p_c)$ is less than TC, the number of images MC with the value of the most frequent color $C(p_{c+j})$ continuously less than TC after the image frame number p is calculated. When MC is greater than a preset threshold TM1 (for example, TM1=5) (in order to remove the effect of uneven light, whether the value of the most frequent color meet the preset threshold TM1 is determined), the capsule has entered the body of subject. The image frame number p is recorded as the initial position 1; $p_{c+j}$ represents the image after $p_c$. The value of j is [1, M], wherein M=preset threshold TM1. The initial position 1 is the first image captured in vivo.

Whether the capsule endoscope is outside the body is determined based on the area ratio sequences of the most frequent color $S(p_1, p_2, \ldots, p_i, \ldots, p_N)$ to obtain the initial position 2. The initial position 2 is obtained by: process from the $N^{th}$ image forward to determine whether the area ratio of the most frequent color in the frame number $p_s$ is greater than a set threshold TS (for example, TS=0.5) (In the body, the proportion of red part of the capsule endoscopic image is larger; whereas outside the body, the proportion of red part of the capsule endoscopic image is smaller). When the area ratio of the most frequent color $S(p_s)$ is greater than the set threshold TS, the number of images MS with the area ratio of the most frequent color $S(p_{s-q})$ continuously greater than TS ahead of the image frame number $p_s$ is calculated. When MS is greater than a set threshold TM2 (for example, TM2=5), the capsule endoscopic image is an in vitro image. The image frame number $p_s$ is recorded as the initial position 2; $p_{s-q}$ represents the image ahead of $p_s$. The value of s is [1, $M_a$], wherein $M_a$=TM2. The capsule endoscopic images ahead of the initial position 2 are in vitro images.

Figure 2:
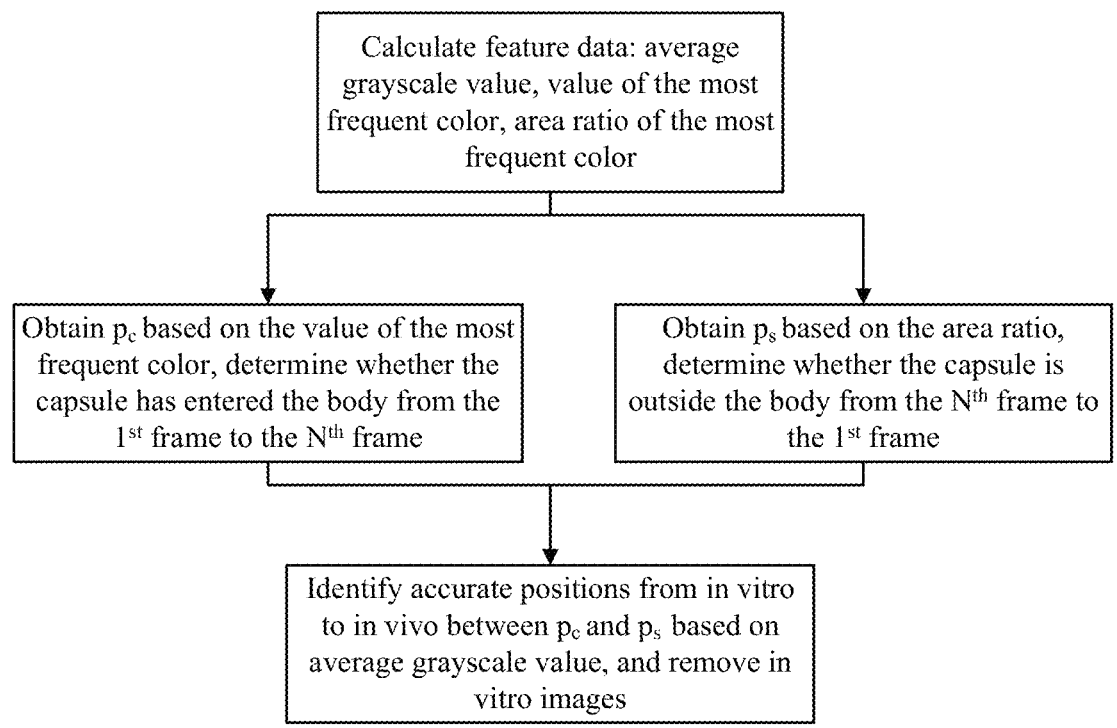
FIG. 2 shows a flowchart of one embodiment of a method for identification of in vitro images.

As shown in FIG. 2, the determination of whether capsule endoscope has entered the body of subject based on the value sequences of the most frequent color and the determination of whether capsule endoscope is outside the body of subject based on the area ratio sequences of the most frequent color are performed concurrently to reduce time and improve efficiency.

From the image frame number $p_s$ to the image frame number $p_c$, in-vitro images are identified based on changes in the average grayscale values of the RGB channels. The in-vitro images are identified by: calculate the changes in average grayscale values of the RGB channels from the image frame number $p_s$ to the image frame number $p_c$ by a formula of $D^o(p_m)=M^o(p_m)-M^o(p_{m+1})$, wherein, o represents channel and the o channel comprises channel R, channel G and channel B; $p_m$ is an image frame number between $p_s$ and $p_c$ and the value of m is [s,c-1], wherein, s is the frame number $p_s$ and c-1 is the frame number $p_c$; determine whether the changes in average grayscale values of RGB channels $D^R(p_m)$, $D^G(p_m)$ and $D^B(p_m)$ comply with a set threshold TD. When $D^R(p_m)$<TD, $D^G(p_m)$<TD and $D^B(p_c)$<TD, the image frame number $p_m$ nearest to the image frame number p is the dividing position for in-vivo images and in vitro images. The capsule endoscopic images ahead of the frame number $p_m$ are all in vitro images and can be removed.

In one embodiment, the determination of whether capsule endoscope has entered the body of subject based on the value sequences of the most frequent color $C(p_1, p_2, \ldots, p_i, \ldots, p_N)$ and the determination of whether capsule endoscope is outside the body of subject based on the area ratio sequences of the most frequent color $S(p_1, p_2, \ldots, p_i, \ldots, p_N)$ are performed concurrently to reduce time and improve efficiency.

In one embodiment, the invalid image removal module 2 further processes the capsule endoscopic images from which the in vitro images have been removed to remove invalid images, wherein the invalid images are images which brightness is not in the preset brightness range. The invalid images are removed by:

Convert the capsule endoscopic RGB images from which in vitro images have been removed to grayscale image gray, and judge each pixel gray(x,y) of the grayscale image gray. When gray(x,y)>YH, the current pixel is too bright; when gray (x,y)<YL, the current pixel is too dark. YH and YL are manually set empirical parameters (for example, YH=220, YL=50). Tally the sum of number of too bright and too dark pixels SHL; SHL=sYL+sYH, wherein sYL represents the number of dark pixels and sYH represents the number of bright pixels; when SHL>ST, the current grayscale image gray is too bright or too dark and is needed to be removed; when sYL>sYH, the grayscale image is too dark, otherwise, the grayscale image is too bright. ST is a manually set empirical parameter, related to the grayscale image size. ST=0.7*SI, wherein SI is the total number of pixels in the grayscale image.

Figure 3:
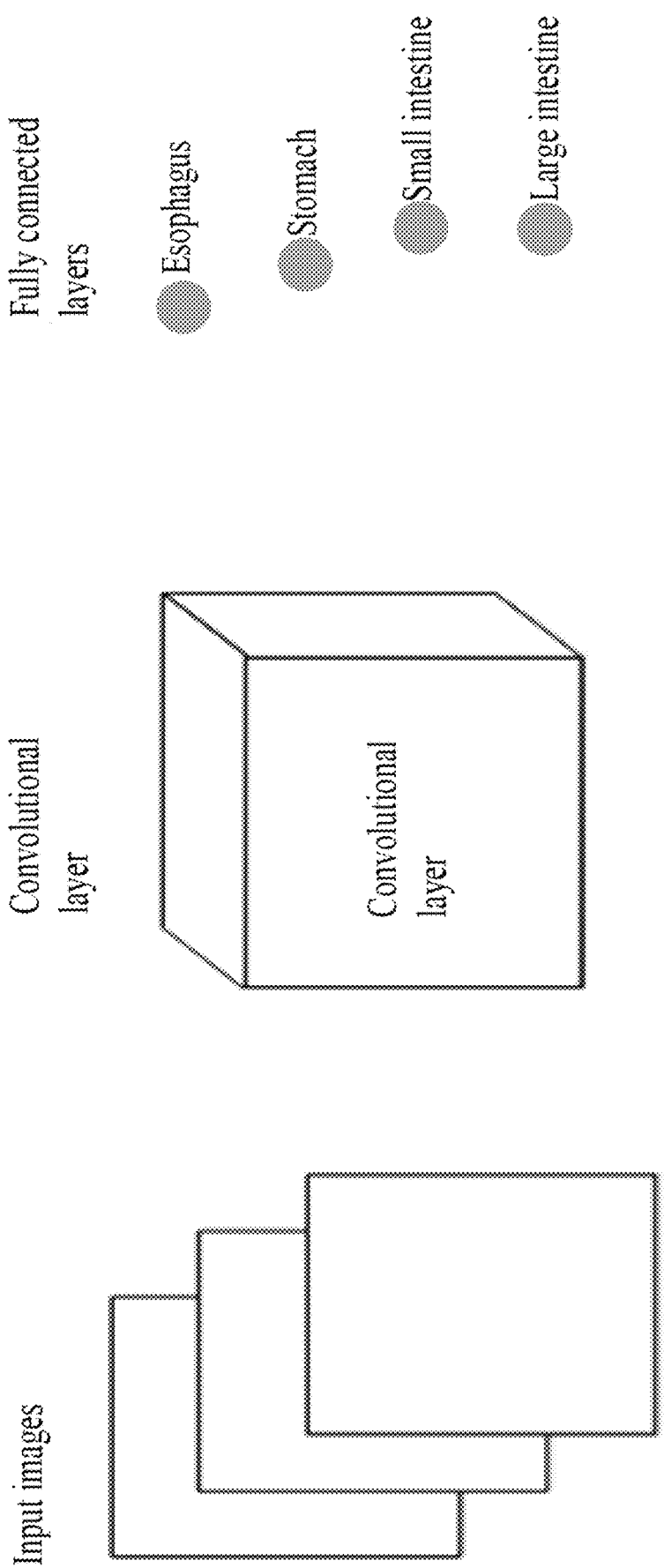
FIG. 3 shows a deep learning model for digestive tract images classification.

The digestive tract image classification module 3 uses a deep learning method based on a Convolutional Neural Network (CNN) model (such as goolenet) to classify the capsule endoscopic images according to different parts of the digestive tract. The deep learning method extracts image features by the CNN model, as shown in FIG. 3. SoftMax function is used in fully connected layers to classify the features of the capsule endoscopic images. As a result, the digestive tract is classified into esophagus, stomach, small intestine, and large intestine.

Figure 4:
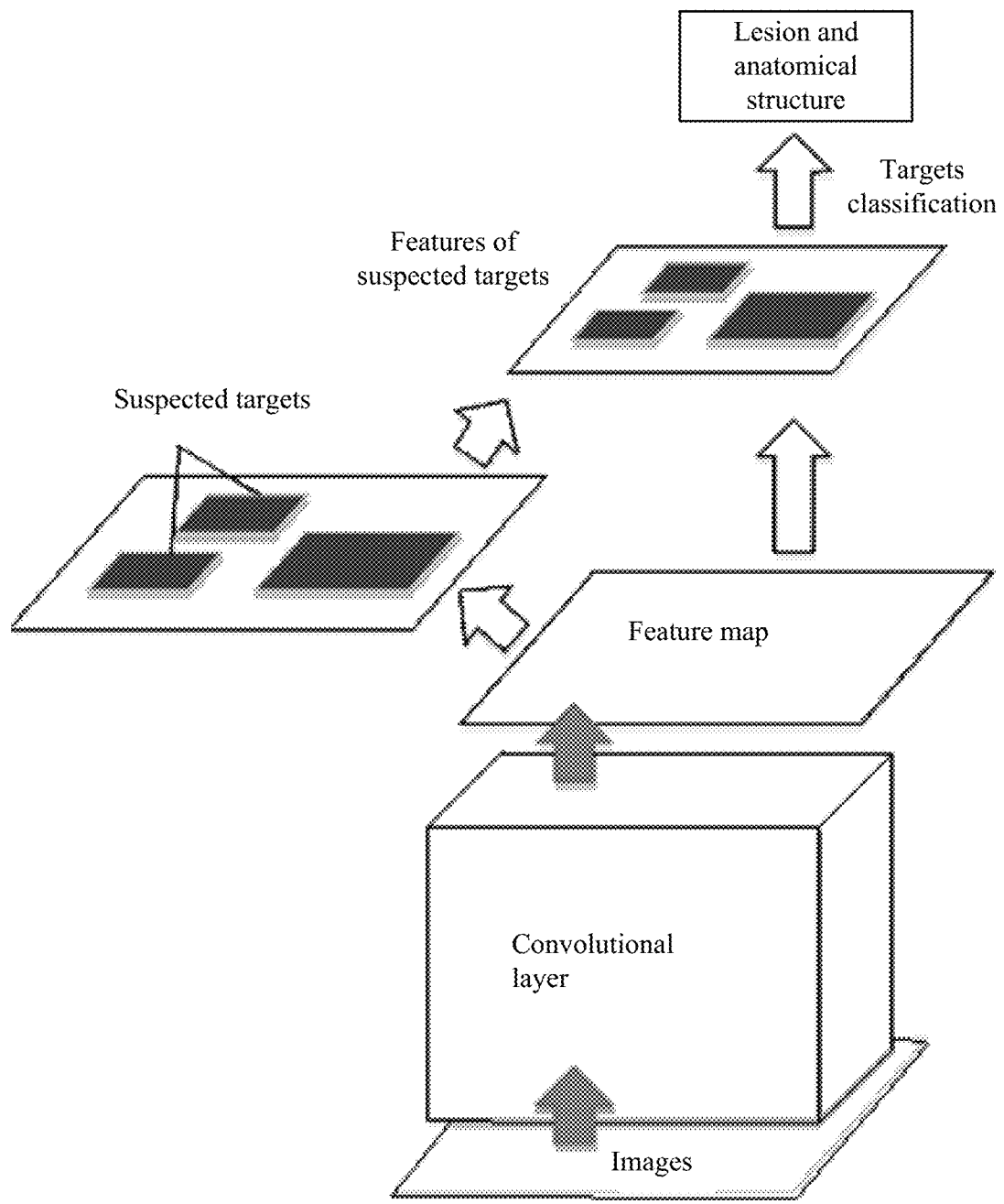
FIG. 4 shows a deep learning model for digestive tract images target identification.

The lesion and anatomical structure identification module 4 uses a deep learning method to identify lesion and anatomical structure in the capsule endoscopic images. As shown in FIG. 4, the feature map is calculated through convolutional layer, and the target positions of the suspected lesion and anatomical structure are selected on the feature map. Then, the features of suspected targets are extracted and classified to obtain the lesion and anatomical structures and their classifications.

Figure 5:
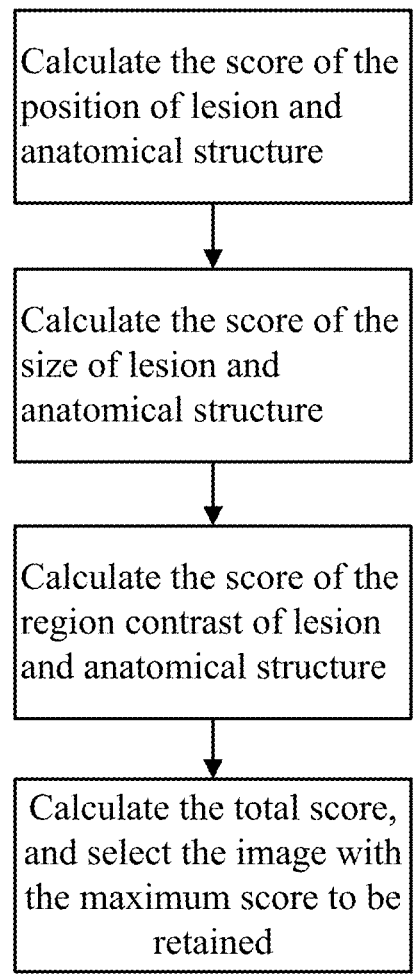
FIG. 5 shows a flowchart of one embodiment of a method for removal of lesion and anatomical structure redundant images.

In one embodiment, for a lesion and anatomical structure, multiple images can be captured continuously. In order to reduce the number of images to be read by doctors, redundant images need to be removed, with clearer images of lesion and anatomical structure retained. The lesion and anatomical structure redundant image removal module 5 identifies lesion and anatomical structure images sequences from the capsule endoscopic image according to the lesion and anatomical structure, and retains images from the lesion and anatomical structure image sequences based on the position, size and contrast characteristics of lesion and anatomical structure. The specific steps for retaining the images are as follows, as shown in FIG. 5:

The score RP of the position of lesion and anatomical structure is calculated in each lesion and anatomical structure image of the lesion and anatomical structure images sequence. The score RP represents the distance from lesion and anatomical structure to the center of corresponding image. The score RP is calculated as follows:

$$RP_i = 1 - \frac{\sqrt{\left(lx_i - \frac{W}{2}\right)^2 + \left(ly_i - \frac{H_1}{2}\right)^2}}{\frac{\sqrt{W^2 + H_1^2}}{2}},$$

wherein, W and $H_1$ represent the width and height of the lesion and anatomical structure image, i represents the serial number in the lesion and anatomical structure images sequence, $RP_i$ represents the score of the position of lesion and anatomical structure in the $i^{th}$ image, and $lx_i$ and $ly_i$ represent the center coordinates of the position of lesion and the anatomical structure in the $i^{th}$ lesion and anatomical structure image. The closer the lesion and anatomical structure are to the center of corresponding image, the higher score RP the image can be obtained, and it needs to retain the image; conversely, the farther the lesion and anatomical structure are to the center of corresponding image, the lower score RP the image can be obtained, and it needs to retain the image.

The score RS of the size of lesion and anatomical structure is calculated in each lesion and anatomical structure image of the lesion and anatomical structure images sequence. The score RS is calculated as follows:

$$RS_i = SW_i \times SH_i$$

wherein, $RS_i$ represents the score of the size of lesion and anatomical structure in the $i^{th}$ lesion and anatomical structure image of the lesion and anatomical structure images sequence, and $SW_i$ and $SH_i$ represent the width and height of lesion and anatomical structure in the $i^{th}$ lesion and anatomical structure image. The score RS is normalized to [0, 1]. The bigger size the lesion and anatomical structure region has, the higher score RS the image can be obtained, and it needs to retain the image; conversely, the smaller size the lesion and anatomical structure region has, the lower score RS the image can be obtained, and it needs to retain the image.

The score RC of the region contrast of lesion and anatomical structure is calculated in each lesion and anatomical structure image of the lesion and anatomical structure images sequence. The score RC is calculated as follows:

$$RC_i = \sum_{\delta} \delta(j,k)^2 P_{\delta}(j,k)$$

Wherein, $RC_i$ represents the score of region contrast of lesion and anatomical structure in the $i^{th}$ lesion and anatomical structure image of the lesion and anatomical structure images sequence, $\delta(j,k) = |gray(j) - gray(k)|$ represents the grayscale difference between neighboring pixels j and k, and $P_{\delta}(j,k)$ represents the probability of occurrence of the grayscale difference $\delta(j,k)$. The score RC is normalized to [0, 1]. The higher contrast the lesion and anatomical structure region has, the bigger score RC the image can be obtained, and it needs to retain the image; conversely, the lower contrast the lesion and anatomical structure region has, the smaller score RC the image can be obtained, and it needs to retain the image.

The total score RT of each lesion and anatomical structure image is calculated. The score RT is calculated as follows: $RT_i = RP_i \times RS_i \times RC_i$, wherein $RT_i$ represents the total score RT of the $i^{th}$ image. The bigger size the lesion and anatomical structure region in the image has, the closer the region is to the center the image, and the higher contrast the region has, the bigger score RT the image can be obtained.

The image with the maximum RT value is selected in the lesion and anatomical structure images sequence as the image to be retained after removal of redundancy. That is, only one most significant image is retained for each lesion and anatomical structure. It is helpful to retain images of the lesions and anatomical structures images close to the center of image, and with a bigger size and higher contrast, to effectively remove redundant images.

A method for preprocessing capsule endoscopic images using the system described above, comprises following blocks. Depending on the embodiment, additional blocks may be added, others removed, and the ordering of the blocks may be changed.

Block S1: The in vitro image removal module 1 removes in vitro images from the capsule endoscopic images based on average grayscale values of the capsule endoscopic images, values of the most frequent color of the capsule endoscopic images, and area ratio of the most frequent color of the capsule endoscopic images, and outputs the removed capsule endoscopic images to the invalid image removal module 2.

The in vitro images are removed from the capsule endoscopic image data as follows:

First, the in vitro image removal module 1 processes the first N frames of the capsule endoscopic images to obtain the average grayscale value sequences of RGB channels: $M^R(p_1, p_2, \ldots, p_i, \ldots, p_N)$, $M^G(p_1, p_2, \ldots, p_i, \ldots, p_N)$, $M^B(p_1, p_2, \ldots, p_i, \ldots, p_N)$, the value sequences of the most frequent color $C(p_1, p_2, \ldots, p_i, \ldots, p_N)$, and the area ratio sequences of the most frequent color $S(p_1, p_2, \ldots, p_i, \ldots, p_N)$. $p_i$ is image frame number.

The in vitro image removal module 1 determines whether the capsule endoscope has entered the body based on the value sequences of the most frequent color $C(p_1, p_2, \ldots, p_i, \ldots, p_N)$ to obtain the initial position 1. The initial position is obtained by: determine whether the value of the most frequent color $C(p_c)$ in the image frame number of $p_c$ is less than the set threshold TC. When the value of the most frequent color $C(p_c)$ is less than TC, the number of images MC with the value of the most frequent color $C(p_{c+j})$ continuously less than TC after the image frame number $p_c$ is calculated. When MC is greater than a preset threshold TM1 (for example, TM1=5), the capsule has entered the body of subject. The image frame number $p_c$ is recorded as the initial position 1; $p_{c+j}$ represents the image after $p_c$. The value of j is [1, M], wherein M=threshold TM1. The initial position 1 is the first image captured in vivo.

The in vitro image removal module 1 determines whether the capsule endoscope is outside the body based on the area ratio sequences of the most frequent color $S(p_1, p_2, \ldots, p_i, \ldots, p_N)$ to obtain the initial position 2. The initial position 2 is obtained by: process from the $N^{th}$ image forward to determine whether the area ratio of the most frequent color in the frame number P is greater than the set threshold TS (for example, TS=0.5). When the area ratio of the most frequent color $S(p_s)$ is greater than the set threshold TS, the number of images MS with the area ratio of the most frequent color $S(p_{s-q})$ continuously greater than TS ahead of the image frame number p is calculated. When MS is greater than a set threshold TM2 (for example, TM2=5), the capsule endoscopic image is an in vitro image. The image frame number $p_s$ is recorded as the initial position 2; $p_{s-q}$ represents the image ahead of $p_s$. The value of s is $[1, M_a]$, wherein $M_a$=TM2. The capsule endoscopic images ahead of the initial position 2 are in vitro images.

From the image frame number $p_s$ to the image frame number $p_c$, in-vitro images are identified based on changes in the average grayscale values of the RGB channels. The in-vitro images are identified by: calculate the changes in average grayscale values of the RGB channels from the image frame number $p_s$ to the image frame number $p_c$ by a formula of $D^o(p_m)=M^o(p_m)-M^o(p_{m+1})$, wherein, o represents channel and the o channel comprises channel R, channel G and channel B; $p_m$ is an image frame number between $p_s$ and $p_c$ and the value of m is [s,c-1], wherein, s is the frame number $p_s$ and c-1 is the frame number $p_c$; determine whether the changes in average grayscale values of RGB channels $D^R(p_m)$, $D^G(p_m)$ and $D^B(p_m)$ comply with the set threshold TD (for example, TD=15). When $D^R(p_m)$< TD, $D^G(p_m)$<TD and $D^B(p_m)$<TD, the image frame number $p_m$ nearest to the image frame number $p_s$ is the dividing position for in-vivo and in vitro images. The capsule endoscopic images ahead of the frame number $p_m$ are all in vitro images and can be removed.

Block S2: The invalid image removal module 2 further processes the capsule endoscopic images from which the in vitro images have been removed to remove the invalid images, wherein the invalid images are images which brightness is not in the preset brightness range. The invalid images are removed by:

Convert the capsule endoscopic RGB image from which in vitro images have been removed to grayscale image gray, and judge each pixel gray(x,y) of the grayscale image gray. When gray(x,y)>YH, the current pixel is too bright; when gray (x,y)<YL, the current pixel is too dark. YH and YL are manually set empirical parameters (for example, YH=220, YL=50). Tally the sum of number of too bright and too dark pixels SHL; SHL=sYL+sYH, wherein sYL represents the number of dark pixels and sYH represents the number of bright pixels; when SHL>ST, the current grayscale image gray is too bright or too dark and needs to be removed; when sYL>sYH, the image is too dark, otherwise, the image is too bright. ST is a manually set empirical parameter, related to the grayscale image size. ST=0.7*SI, wherein SI is the total number of pixels in the grayscale image.

Block S3: The digestive tract image classification module 3 uses a deep learning method based on a Convolutional Neural Network (CNN) model (such as goolenet) to classify the capsule endoscopic images according to different parts of the digestive tract.

Block S4: The lesion and anatomical structure identification module 4 uses a deep learning method to identify lesion and anatomical structure in the capsule endoscopic images.

Block S5: The lesion and anatomical structure redundant image removal module 5 identifies lesion and anatomical structure images sequences from the capsule endoscopic image according to the lesion and anatomical structure, and retains images from the lesion and anatomical structure image sequences based on the position, size and contrast characteristics of lesion and anatomical structure. The specific steps for retaining the images are as follows:

The lesion and anatomical structure redundant image removal module 5 calculates the score RP of the position of lesion and anatomical structure in each lesion and anatomical structure image of the lesion and anatomical structure images sequence. The score RP represents the distance from lesion and anatomical structure to the center of corresponding image. The score RP is calculated as follows:

$$RP_i = 1 - \frac{\sqrt{\left(lx_i - \frac{W}{2}\right)^2 + \left(ly_i - \frac{H_1}{2}\right)^2}}{\frac{\sqrt{W^2 + H_1^2}}{2}},$$

wherein, W and $H_1$ represent the width and height of the lesion and anatomical structure image, i represents the serial number in the lesion and anatomical structure images sequence, $RP_i$ represents the score of the position of lesion and anatomical structure in the $i^{th}$ image, and $lx_i$ and $ly_i$ represent the center coordinates of the position of lesion and the anatomical structure in the $i^{th}$ lesion and the anatomical structure image. The closer the lesion and anatomical structure are to the center of corresponding image, the higher the score RP of the image can be; conversely, the lower the score RP of the image can be.

The lesion and anatomical structure redundant image removal module 5 calculates the score RS of the size of lesion and anatomical structure in each lesion and anatomical structure image of the lesion and anatomical structure images sequence. The score RS is calculated as follows:

$$RS_i = SW_i \times SH_i$$

wherein, $RS_i$ represents the score of the size of lesion and anatomical structure in the $i^{th}$ lesion and anatomical structure image of the lesion and anatomical structure images sequence, and $SW_i$ and $SH_i$ represent the width and height of lesion and anatomical structure in the $i^{th}$ lesion and anatomical structure image. The score RS is normalized to [0, 1].

The lesion and anatomical structure redundant image removal module 5 calculates the score RC of the region contrast of lesion and anatomical structure in each lesion and anatomical structure image of the lesion and anatomical structure images sequence. The score RC is calculated as follows:

$$RC_i = \sum_\delta \delta(j, k)^2 P_\delta(j, k)$$

Wherein, $RC_i$ represents the score of region contrast of lesion and anatomical structure in the $i^{th}$ lesion and anatomical structure image of the lesion and anatomical structure images sequence, $\delta(j,k)=|gray(j)-gray(k)|$ represents the grayscale difference between neighboring pixels j and k, and $P_\delta(j,k)$ represent the probability of occurrence of the grayscale difference $\delta(j,k)$. The score RC is normalized to [0, 1].

The lesion and anatomical structure redundant image removal module 5 calculates the total score RT of each lesion and anatomical structure image. The score RT is calculated as follows:

$$RT_i = RP_i \times RS_i \times RC_i,$$

wherein $RT_i$ represents the total score RT of the $i^{th}$ image.

The lesion and anatomical structure redundant image removal module 5 selects the image with the maximum RT value in the lesion and anatomical structure images sequence as the image to be retained after removal of redundancy. That is, only one most significant image is retained for each lesion and anatomical structure. It is helpful to retain images of the lesions and anatomical structures images close to the center of image, with a bigger size and higher contrast, to effectively remove redundant images.

All of the processes described above may be embodied in, and fully automated via, functional code modules executed by one or more general purpose processors of computing devices. The code modules may be stored in any type of non-transitory readable medium or other storage device. Some or all of the methods may alternatively be embodied in specialized hardware. Depending on the embodiment, the non-transitory readable medium may be a hard disk drive, a compact disc, a digital video disc, a tape drive or other suitable storage medium.

Although certain disclosed embodiments of the present disclosure have been specifically described, the present disclosure is not to be construed as being limited thereto.

Various changes or modifications may be made to the present disclosure without departing from the scope and spirit of the present disclosure.

What is claimed is:

1. A capsule endoscopic image preprocessing system, comprising:
   one or more computer processors configured to:
      receive a plurality of capsule endoscopic images captured by a wireless capsule endoscope;
      remove in vitro images from the capsule endoscopic images based on average grayscale values of the capsule endoscopic images, values of the most frequent color of the capsule endoscopic images, and area ratio of the most frequent color of the capsule endoscopic images;
      remove invalid images from the capsule endoscopic images from which the in vitro images have been removed, wherein the invalid images are images for which brightness is not in a preset brightness range;
      classify the capsule endoscopic images according to different parts of the digestive tract;
      identify lesion and anatomical structures in the classified capsule endoscopic images; and
      remove redundant lesion and anatomical structure images according to the lesion and anatomical structures.

2. The system of claim 1, wherein the one or more computer processors are further configured to calculate the average grayscale value of the capsule endoscopic image by:

$$M^o = \frac{1}{W \times H_1} \sum_{x=1}^{W} \sum_{y=1}^{H_1} I^o(x, y),$$

wherein, W and $H_1$ represent the width and height of the capsule endoscopic image, $I^o(x, y)$ represents the grayscale value of o channels at the position image coordinates x, y, o channels comprise R, G and B channels, and $M^o$ represents the mean value of o channels.

3. The system of claim 1, wherein the value of the most frequent color of the capsule endoscopic image is obtained by the one or more computer processors being configured to:
   convert RGB channels in the capsule endoscopic image into HSV channels using a conversion formula:

$$H = \begin{cases} 0, & \text{if max} = \text{min} \\ 60 \times \frac{G-B}{\text{max}-\text{min}}, & \text{if max} = r \text{ and } g \geq b \\ 60 \times \frac{G-B}{\text{max}-\text{min}} + 360, & \text{if max} = r \text{ and } g < b \\ 60 \times \frac{B-R}{\text{max}-\text{min}} + 120, & \text{if max} = g \\ 60 \times \frac{R-G}{\text{max}-\text{min}} + 240, & \text{if max} = b \end{cases},$$

wherein, max represents the maximum value among RGB channels, min represents the minimum value among RGB channels, and H represents the hue value among HSV channels;
   compute statistics for a histogram of the hue (H) among HSV channels using a statistical formula:

$$\text{hist}_k(H(x,y)) = \text{hist}_{k-1}(H(x,y)) + 1,$$

wherein, hist represents image histogram, H(x,y) represents the value of hue H at the position (x,y), k represents iterations (k<NUM, NUM represents the number of image pixels);
   perform median filtering for the histogram hist(H(x,y)) of hue (H) among HSV channels to remove interference; and
   obtain a position corresponding to the maximum value Gaussian coefficient of the filtered histogram hist(H(x, y)) wherein the value of the color corresponding to the position is the value of the most frequent color of the capsule endoscopic image.

4. The system of claim 3, wherein the maximum value Gaussian coefficient of the filtered histogram hist(H(x,y)) is calculated by the one or more computer processors being configured to:
   perform non-linear least-square fitting for the histogram hist(H(x,y)) with Gaussian model using a fitting formula:

$$f(hist) = \sum_{k=1}^{X} a_k e^{-\left(\frac{hist-c_k}{b_k}\right)^2},$$

wherein, $a_k$ represents coefficient of the $k^{th}$ Gaussian model, and the value of k is between 1 and X, $b_k$ represents variance of the $k^{th}$ Gaussian model, X represents the number of Gaussian models, and $c_k$ corresponding to the maximum coefficient $a_k$ is the value of the most frequent color of the capsule endoscopic image.

5. The system of claim 4, wherein the area ratio of the most frequent color of the capsule endoscopic image is obtained by the one or more computer processors being configured to:
   binarize the hue H in HSV channels to obtain a binary image HB, wherein the threshold of binarization is TH;

set the binary image to 1 as in vitro image when a binarization value of the binary image is greater than TH;

set the binary image to 0 as in vivo image when a binarization value of the binary image is not greater than TH;

wherein the area ratio of the most frequent color is calculated by:

$$S = \frac{1}{W \times H_1} \sum_{x=1}^{W} \sum_{y=1}^{H_1} HB(x, y),$$

wherein, W and $H_1$ represent the width and height of the binary image, x and y represent pixel coordinates, and HB represents the binarized image.

6. The system of claim 5, wherein the in vitro images are removed from the capsule endoscopic images by the one or more computer processors being configured to:

process the first N frames of images to obtain the average grayscale value sequences of RGB channels $M^R(p_1, p_2, \ldots, p_i, \ldots, p_N)$, $M^G(p_1, p_2, \ldots, p_i, \ldots, p_N)$, and $M^B(p_1, p_2, \ldots, p_i, \ldots, p_N)$, value sequences of the most frequent color $C(p_1, p_2, \ldots, p_i, \ldots, p_N)$, and the area ratio sequences of the most frequent color $S(p_1, p_2, \ldots, p_i, \ldots, p_N)$, wherein $p_i$ is image frame number;

determine whether the capsule endoscope has entered the body based on the value sequences of the most frequent color $C(p_1, p_2, \ldots, p_i, \ldots, p_N)$ to obtain an initial position 1; wherein the initial position is obtained by the one or more computer processors being configured to: determine whether the value of the most frequent color $C(p_c)$ in the image frame number of $p_c$ is less than a set threshold TC, calculate the number of images MC with the value of the most frequent color $C(p_{c+j})$ continuously less than TC after the image frame number $p_c$ when the value of the most frequent color $C(p_c)$ is less than TC, determines that the capsule has entered the body of subject when MC is greater than a set threshold TM1, and record the image frame number $p_c$ as the initial position 1; wherein $p_{c+j}$ represents the image after $p_c$, and the value of j is in [1, M];

determine whether the capsule endoscope is outside the body based on the area ratio sequences of the most frequent color $S(p_1, p_2, \ldots, p_i, \ldots, p_N)$ to obtain an initial position 2; wherein the initial position 2 is obtained by the one or more computer processors being configured to: process from the $N^{th}$ image forward to determine whether the area ratio of the most frequent number in the frame number $p_s$ is greater than a set threshold TS, calculate the number of images MS with the area ratio of the most frequent color $S(p_{s-q})$ continuously greater than TS ahead of the image frame number $p_s$ when the area ratio of the most frequent color $S(p_s)$ is greater than the set threshold TS, determine that the image is an in vitro image when MS is greater than a set threshold TM2, and record the image frame number $p_s$ as the initial position 2; wherein $p_{s-q}$ represents the image ahead of $p_s$, and the value of s is in [1, $M_a$], wherein $M_a$=TM2;

identify in-vitro images based on changes in average grayscale values of the RGB channels from the image frame number $p_s$ to the image frame number $p_c$, wherein the in-vitro images are identified by the one or more computer processors being configured to: calculate the changes in average grayscale values of the RGB channels from the image frame number $p_s$ to the image frame number $p_c$ by a formula of $D^o(p_m)=M^o(p_m)-M^o(p_{m+1})$, wherein, o represents channel and the o channel comprises channel R, channel G and channel B; $p_m$ is an image frame number between $p_s$ and $p_c$, and the value of m is in [s,c−1], in which, s is the frame number $p_s$ and c−1 is the frame number $p_c$; and determine whether the changes in average grayscale values of RGB channels $D^R(p_m)$, $D^G(p_m)$ and $D^B(p_m)$ comply with a set threshold TD, determine that the image frame number $p_m$ nearest to the image frame number $p_s$ is the dividing position for in-vivo and in vitro images when $D^R(p_m)$<TD, $D^G(p_m)$<TD and $D^B(p_m)$<TD, and the images ahead of the frame number $p_m$ are in vitro images.

7. The system of claim 6, wherein the one or more computer processors are further configured to concurrently perform the determination of whether the capsule endoscope has entered the body of subject based on the value sequences of the most frequent color $C(p_1, p_2, \ldots, p_i, \ldots, p_N)$ and the determination of whether the capsule endoscope is outside the body of subject based on the area ratio sequences of the most frequent color $S(p_1, p_2, \ldots, p_i, \ldots, p_N)$.

8. The system of claim 6, wherein the invalid images are removed by the one or more computer processors being configured to:

convert the capsule endoscopic RGB image from which in vitro images have been removed to grayscale image gray, determine that a pixel is bright pixel when pixel gray(x,y) of the grayscale image gray is greater than YH, determine that a pixel is dark pixel when pixel gray(x,y) of the grayscale image gray is less than YL, tally the sum of number of bright pixels and dark pixels SHL, wherein SHL=sYL+sYH, in which sYL represents the number of dark pixels and sYH represents the number of bright pixels; and remove the grayscale image gray when SHL is greater than ST, wherein ST=0.7*SI, in which SI is the total number of pixels in the grayscale image.

9. The system of claim 6, wherein the one or more computer processors are further configured to identify lesion and anatomical structure images sequences from the capsule endoscopic images according to the lesion and anatomical structure, and retain images from the lesion and anatomical structure image sequences based on the position, size and contrast characteristics of lesion and anatomical structure, wherein the images are retained by the one or more computer processors being configured to:

calculate the score RP of the position of lesion and anatomical structure in each lesion and anatomical structure image of the lesion and anatomical structure images sequence, wherein the score RP represents the distance from lesion and anatomical structure to the center of corresponding image, and wherein the score RP is calculated by:

$$RP_i = 1 - \frac{\sqrt{\left(lx_i - \frac{W}{2}\right)^2 + \left(ly_i - \frac{H_1}{2}\right)^2}}{\frac{\sqrt{W^2 + H_1^2}}{2}},$$

wherein, W and $H_1$ represent the width and height of the lesion and anatomical structure image, i represents the serial number in the lesion and anatomical structure images sequence, $RP_i$ represents the score of the position of lesion and anatomical structure in the $i^{th}$ image, and $lx_i$ and $ly_i$ represent the center coordinates of the position of lesion and the anatomical structure in the $i^{th}$ lesion and the anatomical structure image;

calculate the score RS of the size of lesion and anatomical structure in each lesion and anatomical structure image of the lesion and anatomical structure images sequence, wherein the score RS is calculated by: $RS_i=SW_i \times SH_i$, wherein, $RS_i$ represents the score of the size of lesion and anatomical structure in the $i^{th}$ lesion and anatomical structure image of the lesion and anatomical structure images sequence, and $SW_i$ and $SH_i$ represent the width and height of lesion and anatomical structure in the $i^{th}$ lesion and anatomical structure image;

calculate the score RC of the region contrast of lesion and anatomical structure in each lesion and anatomical structure image of the lesion and anatomical structure images sequence, and wherein the score RC is calculated by:

$$RC_i = \sum_\delta \delta(j,k)^2 P_\delta(j,k),$$

wherein, $RC_i$ represents the score of region contrast of lesion and anatomical structure in the $i^{th}$ lesion and anatomical structure image of the lesion and anatomical structure images sequence, $\delta(j,k)=|gray(j)-gray(k)|$ represents the grayscale difference between neighboring pixels j and k, and $P_\delta(j,k)$ represent the probability of occurrence of the grayscale difference $\delta(j,k)$;

calculate the total score RT of lesion and anatomical structure image, wherein the total score RT is calculated by:

$RT_i=RP_i \times RS_i \times RC_i$, wherein $RT_i$ represents the total score RT of the $i^{th}$ image; and select the image with the maximum RT value in the lesion and anatomical structure images sequence as the image to be retained after removal of the redundant images.

10. A method for preprocessing capsule endoscopic images, comprising:
receiving a plurality of capsule endoscopic images captured by a wireless capsule endoscope;
removing in vitro images from the capsule endoscopic images based on average grayscale values of the capsule endoscopic images, values of the most frequent color of the capsule endoscopic images, and area ratio of the most frequent color of the capsule endoscopic images;
removing invalid images from the capsule endoscopic images from which the in vitro images have been removed, wherein the invalid images are images for which brightness is not in a preset brightness range;
classifying the capsule endoscopic images according to different parts of the digestive tract;
identifying lesion and anatomical structures in the classified capsule endoscopic images; and
removing redundant lesion and anatomical structure images according to the lesion and anatomical structures.

11. The method of claim 10 comprising calculating the average grayscale value of the capsule endoscopic image by:

$$M^o = \frac{1}{W \times H_1} \sum_{x=1}^{W} \sum_{y=1}^{H_1} I^o(x,y),$$

wherein, W and $H_1$ represent the width and height of the capsule endoscopic image, $I^o(x,y)$ represents the grayscale value of o channels at the position image coordinates x, y, o channels comprise R, G and B channels, and $M^o$ represents the mean value of o channels.

12. The method of claim 10 comprising obtaining the value of the most frequent color of the capsule endoscopic image by:
converting RGB channels in the capsule endoscopic image into HSV channels using a conversion formula:

$$H = \begin{cases} 0, & \text{if max} = \text{min} \\ 60 \times \frac{G-B}{\max-\min}, & \text{if max} = r \text{ and } g \geq b \\ 60 \times \frac{G-B}{\max-\min} + 360, & \text{if max} = r \text{ and } g < b \\ 60 \times \frac{B-R}{\max-\min} + 120, & \text{if max} = g \\ 60 \times \frac{R-G}{\max-\min} + 240, & \text{if max} = b \end{cases}$$

wherein, max represents the maximum value among RGB channels, min represents the minimum value among RGB channels, and H represents the hue value among HSV channels;

computing statistics for a histogram of the hue (H) among HSV channels using a statistical formula:

$\text{hist}_k(H(x,y)) = \text{hist}_{k-1}(H(x,y)) + 1$, wherein, hist represents image histogram, H(x,y) represents the value of hue H at the position (x,y), k represents iterations (k<NUM, NUM represents the number of image pixels);

performing median filtering for the histogram hist(H(x,y)) of hue (H) among HSV channels to remove interference; and obtaining a position corresponding to the maximum value Gaussian coefficient of the filtered histogram hist(H(x,y)), wherein the value of the color corresponding to the position is the value of the most frequent color of the capsule endoscopic image.

13. The method of claim 12 comprising calculating the maximum value Gaussian coefficient of the filtered histogram hist(H(x,y)) by:
performing non-linear least-square fitting for the histogram hist(H(x,y)) with Gaussian model using a fitting formula:

$$f(hist) = \sum_{k=1}^{X} a_k e^{-\left(\frac{hist-c_k}{b_k}\right)^2},$$

wherein, $a_k$ represents coefficient of the $k^{th}$ Gaussian model, and the value of k is between 1 and X, $b_k$ represents variance of the $k^{th}$ Gaussian model, X represents the number of Gaussian models, and $c_k$ corresponding to the maximum coefficient $a_k$ is the value of the most frequent color of the capsule endoscopic image.

14. The method of claim 13 comprising obtaining the area ratio of the most frequent color of the capsule endoscopic image by:
   binarizing the hue H in HSV channels to obtain a binary image HB, wherein the threshold of binarization is TH;
   setting the binary image to 1 as in vitro image when a binarization value of the binary image is greater than TH;
   setting the binary image to 0 as in vivo image when a binarization value of the binary image is not greater than TH;
wherein the area ratio of the most frequent color is calculated by:

$$S = \frac{1}{W \times H_1} \sum_{x=1}^{W} \sum_{y=1}^{H_1} HB(x, y),$$

wherein, W and $H_1$ represent the width and height of the binary image, x and y represent pixel coordinates, and HB represents the binarized image.

15. The method of claim 14 comprising removing the in vitro images from the capsule endoscopic images by:
   processing the first N frames of the capsule endoscopic images to obtain average grayscale value sequences of RGB channels $M^R(p_1, p_2, \ldots, p_i, \ldots, p_N)$ $M^G(p_1, p_2, \ldots, p_i, \ldots, p_N)$ and $M^B(p_1, p_2, \ldots, p_i, \ldots, p_N)$, value sequences of the most frequent color $C(p_1, p_2, \ldots, p_i, \ldots, p_N)$, and area ratio sequences of the most frequent color $S(p_1, p_2, \ldots, p_i, \ldots, p_N)$, wherein $P_i$ is image frame number;
   determining whether the capsule endoscope has entered the body based on the value sequences of the most frequent color $C(p_1, p_2, \ldots, p_i, \ldots, p_N)$ to obtain an initial position 1; wherein the initial position is obtained by: determining whether the value of the most frequent color $C(p_c)$ in the image frame number of $p_c$ is less than a set threshold TC, calculating the number of images MC with the value of the most frequent color $C(p_{c+j})$ continuously less than TC after the image frame number $p_c$ when the value of the most frequent color $C(p_c)$ is less than TC, determining that the capsule has entered the body of subject when MC is greater than a set threshold TM1, and recording the image frame number $p_c$ as the initial position 1, wherein $p_{c+j}$ represents the image after $p_c$, and the value of j is in [1, M];
   determining whether the capsule endoscope is outside the body based on the area ratio sequences of the most frequent color $S(p_1, p_2, \ldots, p_i, \ldots, p_N)$ to obtain an initial position 2; wherein the initial position 2 is obtained by: processing from the $N^{th}$ image forward to determine whether the area ratio of the most frequent color in the frame number $p_s$ is greater than a set threshold TS, calculating the number of images MS with the area ratio of the most frequent color $S(p_{s-q})$ continuously greater than TS ahead of the image frame number $p_s$ when the area ratio of the most frequent color $S(p_s)$ is greater than the set threshold TS, determining that the image is an in vitro image when MS is greater than a set threshold TM2, and recording the image frame number $p_s$ as the initial position 2; wherein $p_{s-q}$ represents the image ahead of $p_s$, and the value of s is in [1, $M_a$], wherein $M_a$=TM2;
   identifying in vitro images based on changes in average grayscale values of the RGB channels from the image frame number $p_s$ to the image frame number $p_c$, wherein the in-vitro images are identified by: calculating the changes in average grayscale values of the RGB channels from the image frame number $p_s$ to the image frame number $p_c$ by a formula of $D^o(p_m)=M^o(p_m)-M^o(p_{m+1})$, wherein, o represents channel and the o channel comprise channel R, channel G and channel B, $p_m$ is an image frame number between $p_s$ and $p_c$, and the value of m is in [s,c−1], in which, s is the frame number $p_s$ and c−1 is the frame number $p_c$; and
   determining whether the changes in average grayscale value of RGB channels $D^R(p_m)$, $D^G(p_m)$ and $D^B(p_m)$ comply with a set threshold TD, and determining that the image frame number $p_m$ nearest to the image frame number $p_s$ is the dividing position for in-vivo and in vitro images when $D^R(p_m)$<TD, $D^G(p_m)$<TD and $D^B(p_m)$<TD, and the images ahead of the frame number $p_m$ are in vitro images.

16. The method of claim 15 comprising performing concurrently the determination of whether the capsule endoscope has entered the body of subject based on the value sequences of the most frequent color $C(p_1, p_2, \ldots, p_i, \ldots, p_N)$ and the determination of whether the capsule endoscope is outside the body of subject based on the area ratio sequences of the most frequent color $S(p_1, p_2, \ldots, p_i, \ldots, p_N)$.

17. The method of claim 15 comprising removing the invalid images by:
   converting the capsule endoscopic RGB image from which in vitro images have been removed to grayscale image gray, determine that a pixel is bright pixel when pixel gray(x,y) of the grayscale image gray is greater than YH,
   determining that a pixel is dark pixel when pixel gray(x,y) of the grayscale image gray is less than YL,
   tallying the sum of number of bright pixels and dark pixels SHL, wherein SHL=sYL+sYH, in which sYL represents the number of dark pixels and sYH represents the number of bright pixels, and
   removing the grayscale image gray when SHL is greater than ST, wherein ST=0.7*SI, in which SI is the total number of pixels in the grayscale image.

18. The method of claim 15 comprising:
   identifying lesion and anatomical structure images sequences from the capsule endoscopic images according to the lesion and anatomical structure; and
   retaining images from the lesion and anatomical structure image sequences based on the position, size and contrast characteristics of lesion and anatomical structure, wherein the images are retained by:
   calculating the score RP of the position of lesion and anatomical structure in each lesion and anatomical structure image of the lesion and anatomical structure images sequence, wherein the score RP represents the distance from lesion and anatomical structure to the center of corresponding image, and wherein the score RP is calculated by:

$$RP_i = 1 - \frac{\sqrt{\left(lx_i - \frac{W}{2}\right)^2 + \left(ly_i - \frac{H_1}{2}\right)^2}}{\frac{\sqrt{W^2 + H_1^2}}{2}},$$

wherein, W and $H_1$ represent the width and height of the lesion and anatomical structure image, i represents the serial number in the lesion and anatomical structure images sequence, $RP_i$ represents the score of the position of lesion and anatomical structure in the $i^{th}$ image, and $lx_i$ and $ly_i$ represent the center coordinates of the position of lesion and the anatomical structure in the $i^{th}$ lesion and the anatomical structure image;

calculating the score RS of the size of lesion and anatomical structure in each lesion and anatomical structure image of the lesion and anatomical structure images sequence, wherein the score RS is calculated by: $RS_i = SW_i \times SH_i$, wherein, $RS_i$ represents the score of the size of lesion and anatomical structure in the $i^{th}$ lesion and anatomical structure image of the lesion and anatomical structure images sequence, and $SW_i$ and $SH_i$ represent the width and height of lesion and anatomical structure in the $i^{th}$ lesion and anatomical structure image;

calculating the score RC of the region contrast of lesion and anatomical structure in each lesion and anatomical structure image of the lesion and anatomical structure images sequence, and wherein the score RC is calculated by:

$$RC_i = \sum_{\delta} \delta(j,k)^2 P_\delta(j,k),$$

wherein, $RC_i$ represents the score of region contrast of lesion and anatomical structure in the $i^{th}$ lesion and anatomical structure image of the lesion and anatomical structure images sequence, $\delta(j,k)=|gray(j)-gray(k)|$ represents the grayscale difference between neighboring pixels j and k, and $P_\delta(j,k)$ represent the probability of occurrence of the grayscale difference $\delta(j,k)$;

calculating the total score RT of lesion and anatomical structure image, wherein the total score RT is calculated by:

$$RT_i = RP_i \times RS_i \times RC_i, \text{ wherein } RT_i \text{ represents the total score } RT \text{ of the } i^{th} \text{ image; and}$$

selecting the image with the maximum RT value in the lesion and anatomical structure images sequence as the image to be retained after removing the redundant images.

19. The system of claim 1, wherein the one or more computer processors are further configured to perform deep learning based on a convolutional neural network model to classify the capsule endoscopic images according to different parts of the digestive tract.

20. The system of claim 1, wherein the one or more computer processors are further configured to perform deep learning to identify the lesion and anatomical structure in the capsule endoscopic images.

* * * * *